US009116080B2

(12) United States Patent
Spampinato et al.

(10) Patent No.: US 9,116,080 B2
(45) Date of Patent: Aug. 25, 2015

(54) COMPRESSION TESTING DEVICE FOR TESTING MATERIALS AUTOMATICALLY

(71) Applicant: NIKE, Inc., Beaverton, OR (US)

(72) Inventors: Juan-Pier A. Spampinato, Aloha, OR (US); Edward F. Wachtel, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/280,380

(22) Filed: May 16, 2014

(65) Prior Publication Data

US 2014/0290377 A1  Oct. 2, 2014

Related U.S. Application Data

(63) Continuation of application No. 13/011,521, filed on Jan. 21, 2011, now Pat. No. 8,766,811.

(51) Int. Cl.
*G01N 3/08* (2006.01)
*G01M 99/00* (2011.01)
*G01N 3/34* (2006.01)

(52) U.S. Cl.
CPC ............... *G01N 3/08* (2013.01); *G01M 99/001* (2013.01); *G01N 3/34* (2013.01); *G01N 3/342* (2013.01)

(58) Field of Classification Search
CPC ....................................................... G01N 8/03
USPC ........................................................... 73/813
See application file for complete search history.

(56) References Cited

U.S. PATENT DOCUMENTS

| 2,245,080 | A | 6/1941 | Pendleton |
| 3,657,921 | A | 4/1972 | Lang |
| 3,786,676 | A | 1/1974 | Korolyshun et al. |
| 4,649,735 | A | 3/1987 | Pihlaja |
| 5,084,486 | A | 1/1992 | Patten et al. |
| 5,092,179 | A | 3/1992 | Ferguson |
| 5,575,078 | A | 11/1996 | Moulton, III |
| 5,913,246 | A | 6/1999 | Simonelli et al. |
| 6,205,863 | B1 | 3/2001 | Ishii et al. |
| 6,267,011 | B1 | 7/2001 | Kurtz et al. |
| 6,283,336 | B1 | 9/2001 | Dwyer et al. |
| 6,882,732 | B2 | 4/2005 | Pavlakos |
| 7,298,876 | B1 | 11/2007 | Marshall et al. |

(Continued)

OTHER PUBLICATIONS

International Preliminary Report on Patentability mailed on Aug. 1, 2013 in connection with PCT Application Serial No. PCT/US2012/021464; 9 pages.

(Continued)

*Primary Examiner* — Lisa Caputo
*Assistant Examiner* — Jamel Williams
(74) *Attorney, Agent, or Firm* — Plumsea Law Group, LLC

(57) ABSTRACT

A compression testing assembly for compression testing of a test material includes a testing stage with a first surface and a second surface. The test material is disposed between the first and second surfaces. The assembly also includes a thickness detector that automatically detects a thickness of the test material. Moreover, the assembly includes an actuator that moves at least one of the first and second surfaces toward the other of the first and second surfaces to compress the test material to a predetermined percentage of the detected thickness of the test material. Additionally, the assembly includes a load detector that detects a compression load of the test material and that detects a change in the compression load over time.

18 Claims, 2 Drawing Sheets

(56) References Cited

U.S. PATENT DOCUMENTS

| | | |
|---|---|---|
| 7,784,355 B2 | 8/2010 | Kawano |
| 8,766,811 B2 * | 7/2014 | Spampinato et al. ......... 340/665 |
| 2002/0007682 A1 | 1/2002 | Arimond et al. |
| 2002/0170360 A1 | 11/2002 | Anand et al. |
| 2004/0144180 A1 | 7/2004 | Imamura |
| 2007/0213419 A1 | 9/2007 | Cao et al. |
| 2007/0260319 A1 | 11/2007 | Reah |
| 2008/0183807 A1 | 7/2008 | Salesky et al. |
| 2010/0204932 A1 | 8/2010 | Sakai |
| 2010/0228156 A1 * | 9/2010 | Valero-Cuevas et al. ..... 600/587 |
| 2012/0060581 A1 * | 3/2012 | Maki .............................. 73/1.08 |

OTHER PUBLICATIONS

Polyurethane Foam Association, Section 4.0, Joint Industry Foam Standards and Guidelines; Published Jul. 1994; accessed on Feb. 24, 2010; www.pfa.org/jifsg/jifsgs4.html, 8 pages.

SITA Foam Tester R-2000; Easy and Repeatable Testing and Monitoring of the Foaming Characteristics of foaming Liquids, accessed on Feb. 24, 2010, www.online-tenslometer.com/produkte/r2000/foam_tester_r2000.html, 2 pages.

International Search Report and Written Opinion dated May 23, 2012, International Application No. PCT/US2012/021464, International Filing Date Jan. 17, 2012.

* cited by examiner

COMPRESSION TESTING DEVICE FOR TESTING MATERIALS AUTOMATICALLY

CROSS REFERENCE TO RELATED APPLICATION(S)

This application is a continuation of co-pending U.S. patent application Ser. No. 13/011,521, filed on Jan. 21, 2011, the disclosure of which is incorporated by reference in its entirety.

FIELD

The present disclosure relates to a compression testing device and, more particularly, relates to a compression testing device for testing materials automatically.

BACKGROUND

Compression testing is performed on a variety of goods. For instance, articles of footwear often include foam midsoles, rubber outsoles, fluid-filled bladders, etc., and these items are often tested to determine how they will perform under compression loading. More specifically, a tool can be used to determine the amount of force it takes to compress the test material to a predetermined amount.

This type of testing can be burdensome. For instance, compression testing is sometimes performed manually, and this process can take a significant amount of time. Also, testing can be especially burdensome if a large number of different materials are tested.

Furthermore, the testing can be inaccurate. For instance, human error, manufacturing tolerances, and the like can contribute to testing inaccuracies.

Still further, it can be difficult and/or burdensome to record test results. Likewise, obtaining these results after testing has been completed can be difficult and/or burdensome.

Accordingly, there remains a need for a compression testing device that simplifies the compression testing process. Also, there remains a need for such a testing device that is more accurate than existing testing devices. Still further, there remains a need for such a testing device, in which test data can be stored and communicated in a convenient manner.

SUMMARY

A compression testing assembly for compression testing of a test material is disclosed that includes a testing stage with a first surface and a second surface. The test material is disposed between the first and second surfaces. The assembly also includes a thickness detector that automatically detects a thickness of the test material. Moreover, the assembly includes an actuator that moves at least one of the first and second surfaces toward the other of the first and second surfaces to compress the test material to a predetermined percentage of the detected thickness of the test material. Additionally, the assembly includes a load detector that detects a compression load of the test material and that detects a change in the compression load over time.

Also, a method of performing a compression test on a test material is disclosed that includes disposing the test material between a first surface and a second surface. The method also includes actuating at least one of the first and second surfaces toward the other of the first and second surfaces and automatically detecting a thickness of the test material. Furthermore, the method includes compressing the test material between the first and second surfaces to a predetermined percentage of the detected thickness of the test material. Still further, the method includes detecting a compression load of the test material and detecting a change in the compression load over time.

Moreover, a compression testing assembly for compression testing of a foam test material for an article of footwear is disclosed. The compression testing device includes a testing stage with a base surface and a probe that is moveable relative to the base surface in a first direction toward and away from the base surface and in a second direction that is substantially perpendicular to the first direction. The foam test material is supported on the base surface, between the base surface and the probe. The assembly includes a position detector that detects a position of the probe relative to the base surface. Also, the assembly includes an actuator that actuates the probe relative to the base surface in the first direction and the second direction, wherein the actuator actuates the probe in the first direction to compress the foam test material. Moreover, the assembly includes a load detector that detects a compression load of the test material and that detects a change in the compression load over time. Additionally, the assembly includes a controller that controls the actuator to actuate the probe toward the base until the load detector detects a load increase, at which point the position detector automatically detects a distance between the base surface and the probe to detect a thickness of the foam test material. The controller further controls the actuator to compress the foam test material to approximately fifty percent of the detected thickness of the foam test material during a first compression, to release the foam test material after the first compression, and to compress the foam test material to approximately fifty percent of the thickness of the foam test material during a second compression, at which point the load detector detects the compression load. The controller further controls the actuator to release the foam test material after the second compression, and to compress the foam test material to approximately fifty percent of the thickness of the foam test material during a third compression, at which point the load detector detects a change in the compression load over time. Furthermore, the assembly includes a communications device for communicating over a communications network the detected compression load and the detected change in the compression load overtime.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
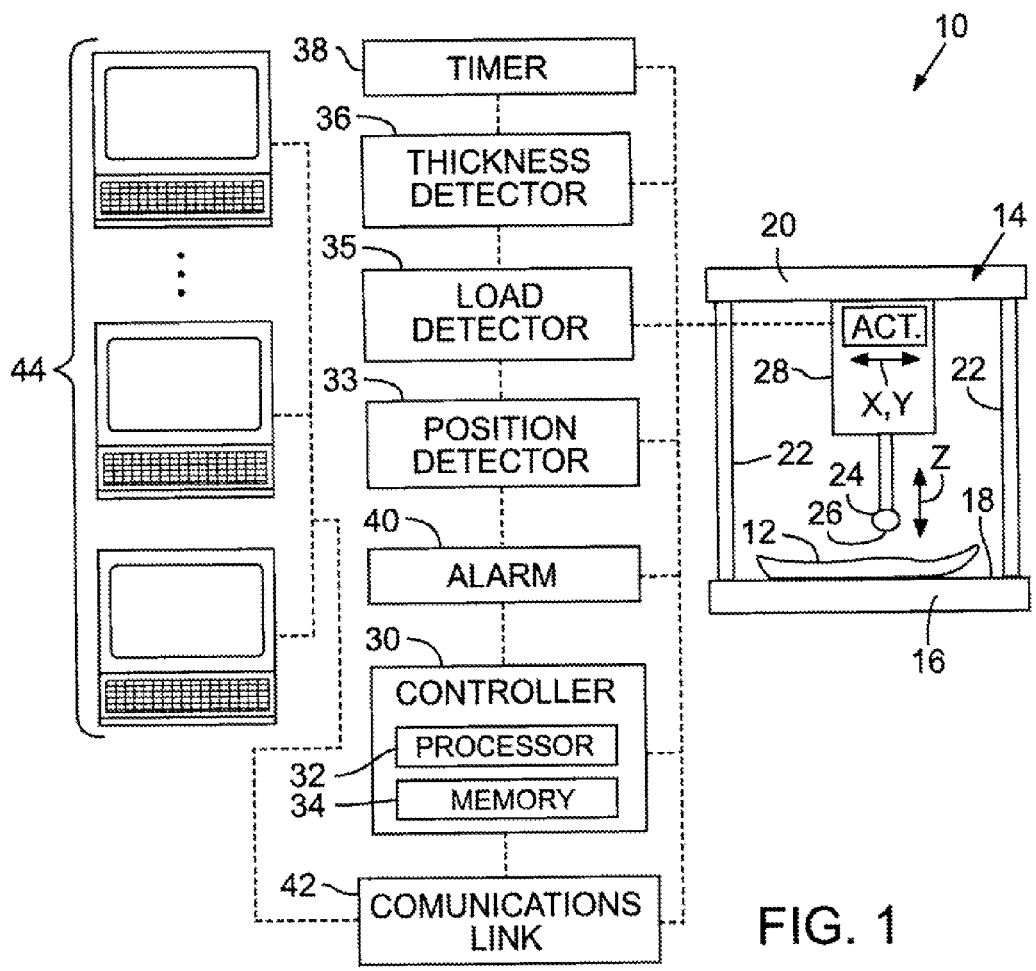
FIG. 1 is a schematic illustration of a compression testing assembly according to various exemplary embodiments of the present disclosure.

Referring initially to FIG. 1, a compression testing assembly 10 is schematically illustrated. The assembly 10 can perform compression testing of a test material 12. The assembly 10 can perform compression testing on any suitable type of test material 12, such as test material 12 for use in connection with an article of footwear (not shown). As such, the test material 12 can be foam, rubber, or other polymeric test material that is included within a midsole, outsole, or upper of a shoe, boot, sandal, or other type of footwear. Moreover, the test material 12 can be a fluid filled bladder that is included within a sole assembly or upper of an article of footwear. However, it will be appreciated that the test material 12 can be of any type of test material and can be employed in any article other than an article of footwear without departing from the scope of the present disclosure.

It will be appreciated that the test material 12 can be of any suitable shape, such as a relatively flat, rectangular sample of test material 12 with a substantially constant thickness. In other embodiments, the test material 12 can vary in thickness across different portions of the test material 12. Moreover, the test material 12 can have substantially consistent compression characteristics (e.g., resistance to resilient deformation) across its entire width, or the compression characteristics of the test material 12 can vary across different portions of the test material 12. As will be discussed, the same testing assembly 10 can perform a variety of compression tests for any test material 12 in a convenient and accurate manner.

As shown in FIG. 1, the testing assembly 10 can include a testing stage 14 with a base 16. The base 16 can be relatively flat and wide and can include a base surface 18. Also, the assembly 10 can include an upper portion 20 and a plurality of legs 22 that support the upper portion 20 above the base surface 18 such that the upper portion 20 is spaced apart at a distance from the base surface 18. In addition, the assembly 10 can include a probe 24 with a probe surface 26. As will be discussed, the distance between the probe surface 26 and the base surface 18 is selectively variable.

The test material 12 can be disposed between the probe surface 26 and the base surface 18. For instance, the test material 12 can be supported on the base surface 18 with the probe 24 suspended above the test material 12. Also, the test material 12 can be retained and secured between the base surface 18 and the probe 24 in any suitable manner. For instance, the test material 12 can be placed on the base surface 18 and held there only by gravity. In other embodiments, the test material 12 can be clamped to the base surface 18, held by a vacuum source, or otherwise fixed to the base surface 18.

Moreover, the testing assembly 10 can include an actuator 28. The actuator 28 can be of any suitable type, such as an electric, pneumatic, hydraulic, or other type of actuator 28. Also, the actuator 28 can include one or more motors, or other types of actuators 28. The actuator 28 can be operably coupled to the probe 24 in order to selectively actuate the probe 24 relative to the base surface 18.

Figure 2:
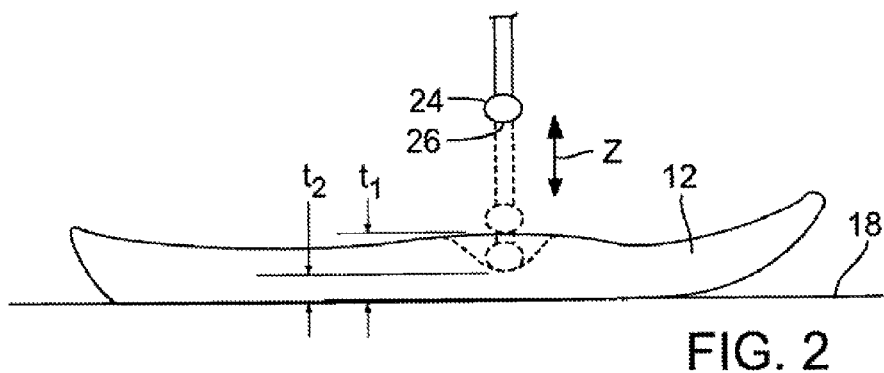
FIG. 2 is a side view of a material being compression tested using the compression testing assembly of FIG. 1.

The actuator 28 can selectively actuate the probe 24 relative to the base surface 18 in any suitable direction. For instance, the actuator 28 can selectively actuate the probe 24 toward and away from the base surface 18, as indicated by the double-headed arrow Z in FIG. 1. Thus, the probe 24 can selectively move in the Z-direction (the first direction) generally parallel to a thickness of the test material 12 as shown in FIG. 2. Furthermore, the actuator 28 can selectively actuate the probe 24 relative to the base surface 18 in a direction that is substantially perpendicular to the Z-direction as indicated by the double headed arrow X-Y in FIG. 1. Thus, as viewed in FIG. 1, the probe 24 can move to the left and right and/or in and out of the page in order to move over different portions of the test material 12.

It will be appreciated that the actuator 26 can selectively actuate the probe 24 and/or the base 16 relative to the other in any suitable direction. For instance, in some embodiments, the base 16 or other part of the assembly 10 can include a conveyor belt or other type of conveyor system for moving the probe 24 and base 16 relative to each other in the X-Y direction, and the actuator 26 can selectively operate the conveyor to move the base surface 16 and probe surface 26 relative to each other and to automatically convey the test material 12 underneath the probe surface 26. Furthermore, the actuator 26 can actuate the base 16 toward and away from the probe 24 in the Z-direction. Moreover, in some embodiments, the assembly 10 can include a plurality of actuators 26, each for individually moving the probe 24 and base 16 relative to each other in any suitable direction. In addition, in some embodiments, the actuator 26 can rotate the probe and base 16 relative to each other about any suitable axis of rotation.

The compression testing assembly 10 can also include a controller 30. The controller 30 can include various components, such as a processor 32, a memory module 34, programmed logic, and other types of devices, and the controller 30 can be included within a personal computer in some embodiments. The controller 30 can be in communication with the actuator 28 for controlling selective actuation of the probe 24. For instance, the controller 30 can control the actuator 28 such that the probe 24 actuates toward the test material 12 (in the Z-direction) to compress the test material 12, and such that the probe 24 subsequently actuates away from the test material 12 (in the Z-direction) to release the test material 12. Moreover, the controller 30 can control the actuator 28 such that the probe 24 moves across the test material 12 (in the X-Y direction), and such that the probe 24 subsequently compresses and releases another portion of the test material 12. As such, the compression testing can be very convenient as will be discussed.

The testing assembly 10 can further include a load detector 35. The load detector 35 can include a conventional load cell and can have any suitable operating compression load range. The load detector 35 can operate to detect a compression load (e.g., compression force, stress, strain, pressure, or other type of compression load) between the base surface 18 and the probe surface 26. Thus, assuming the test material 12 is between the surfaces 18, 26, the load detector 35 can detect the compression load applied to the test material 12 by the probe 24 and the base 16. The load detector 35 can be operably connected to the controller 30 such that the detected compression load data can be stored in the memory module 34.

Additionally, in some embodiments, the testing assembly 10 can include a position detector 33 that is operable for detecting a position of the probe surface 26 relative to the base surface 18. The position detector 33 can be of any suitable type. For instance, the position detector 33 can be in communication with the controller 30 and the actuator 28, and the position of the probe 24 (and thus the probe surface 26) can be calibrated and tracked relative to the base surface 18.

Moreover, the testing assembly 10 can include a thickness detector 36 that is operable to automatically detect a thickness $t_1$ of the test material 12 (FIG. 2). The thickness detector 36 can be of any suitable type, such as an optical-type thickness detector 36 with cameras and other components for automatically detecting the thickness t1 of the material 12.

In other embodiments, the thickness detector 36 is in communication with the position detector 33 and the load detector 35, and information from each allows the thickness detector 36 to determine the thickness $t_1$ of the test material 12. More specifically, as the probe 24 moves toward the test material 12, the position detector 33 continuously monitors the distance (in the Z-direction) between the probe surface 26 and the base surface 18. Then, as the probe surface 26 eventually contacts the test material 12, the load detector 35 will detect an increase in loading (i.e., an "initial load increase"). At the approximate point that the initial load increase is detected, the thickness detector 36 can obtain the distance (in the Z-direction) between the probe surface 26 and the base surface 18 from the position detector 33, which corresponds with the actual thickness $t_1$ of the test material 12 (FIG. 2).

Thus, the thickness $t_1$ of the test material 12 can be detected conveniently and accurately. This feature can be especially useful if the test material 12 varies in thickness and/or if a variety of test materials 12 with different thicknesses are tested.

The compression testing assembly 10 can also compress the test material 12 to any suitable predetermined percentage of the thickness $t_1$ of the test material 12. (As shown in FIG. 2, the testing assembly 10 can compress the test material 12 to the thickness $t_2$.) In some embodiments, the assembly 10 can compress the test material 12 to a thickness h that is approximately equal to between 30% and 70% of the total thickness $t_1$ of the test material 12. Also, the assembly 10 can compress the test material 12 to a thickness $t_2$ that is approximately equal to 50% of the total thickness $t_1$ of the test material 12. The load detector 35 can detect the compression load on the test material 12 when the test material 12 is compressed to this predetermined thickness t2. Accordingly, the indentation force deflection (IDF), the resistance to resilient deformation, viscoelasticity, release/recovery characteristics, or any other related characteristic of the test material 12 can be tested conveniently and accurately.

Also, in some embodiments, the assembly 10 can include a timer 38. The timer 38 can be of any suitable type of device for measuring and detecting an amount of time. As will be discussed, the timer 38 can detect the particular time and date that the test material 12 is being compressed for identifying a particular compression test.

Also, the timer 38 can detect how long the test material 12 has been compressed, and the load detector 35 can detect a change in the compression load over that amount of time, for instance, to measure the viscoelasticity of the test material 12. Moreover, in some embodiments, the timer 38 can detect how long the test material 12 takes to recover after the probe 24 releases the test material 12.

Additionally, the assembly 10 can include an alarm 40. The alarm 40 can include an audible alarm, a visual alarm, a tactile alarm (e.g., a vibrating surface), or any other suitable alarm 40 for indicating that the test material 12 is unacceptable and does not meet certain predetermined limits or standards.

Different test materials 12 can have different predetermined limits/standards for acceptability. For example, it might take X Newtons of force to compress the test material 12 to the thickness h (as detected by the load detector 35), and the particular test material 12 might be acceptable only if X is within a predetermined range or limit. Also, the test material 12 might be acceptable only if the change in X over a predetermined amount of time is within a predetermined range. If X and/or the change in X is outside the predetermined range, then the alarm 40 can output its respective audible, visual, tactile or other alarm signal to indicate that the test material 12 is unacceptable for further use.

Furthermore, the assembly 10 can include a communications device 42 that communicates test data over a communications network 44. For instance, the communications device 42 can provide communication between the controller 30 and the communications network 44 (e.g., over an Internet connection) such that the test data gathered in the memory module 34 can be communicated to remote computers or other devices within the communications network 44. Accordingly, the test data can be accessed relatively easily, even in remote locations.

Figure 3:
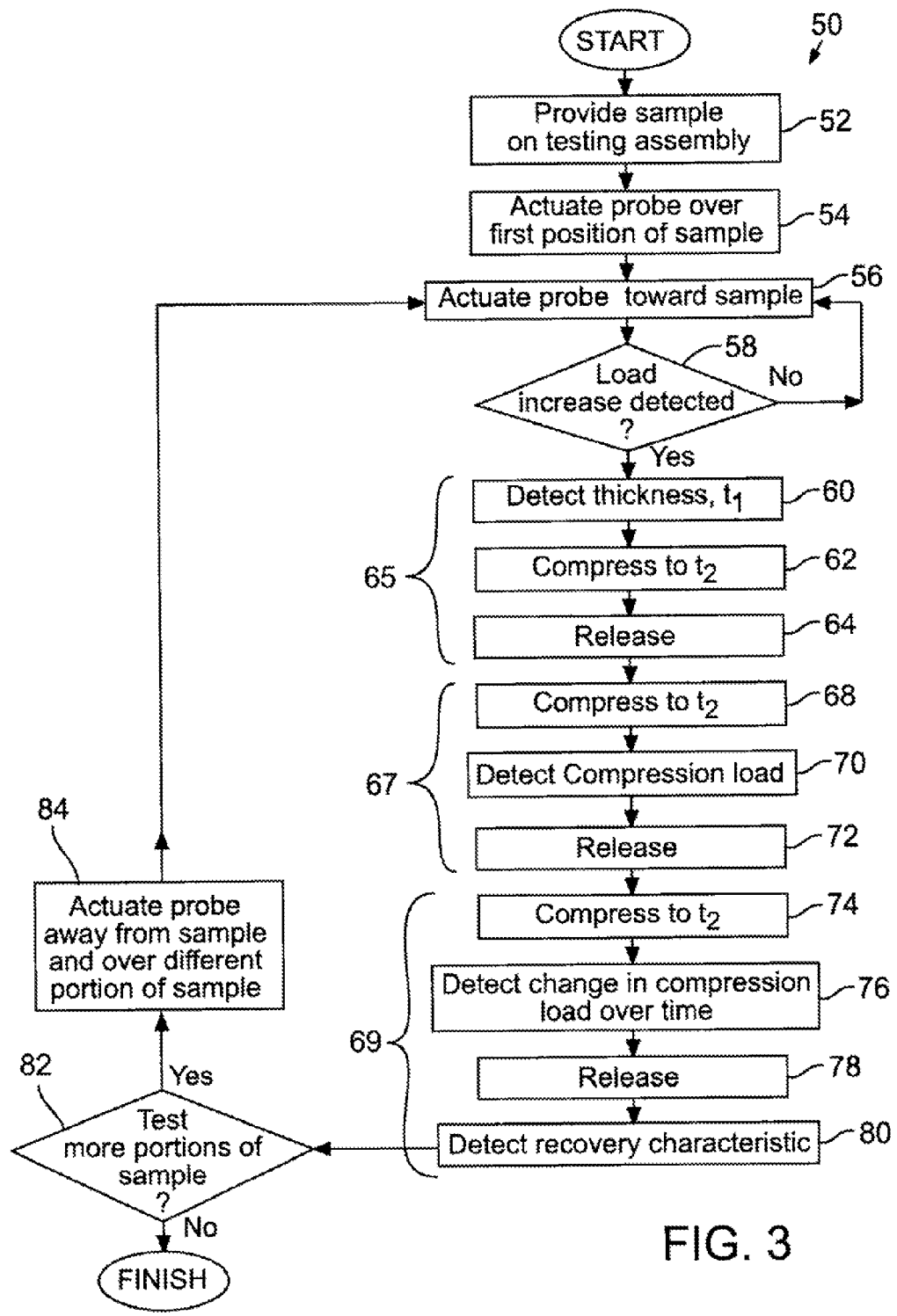
FIG. 3 is a flowchart illustrating an exemplary embodiment of a method of operation of the compression testing assembly of FIG. 1.

Referring now to FIG. 3, an exemplary embodiment of a method 50 of operating the compression testing assembly 10 will be discussed. As shown, the method 50 begins in block 52, wherein the test material 12 is provided on the testing stage 14 between the base surface 18 and the probe surface 26. Then, in block 54, the actuator 28 actuates the probe 24 in the X and/or Y directions, over a predetermined portion of the material 12, and in block 56, the actuator 28 also actuates the probe 24 in the Z direction, toward the material 12.

Next, the thickness $t_1$ (FIG. 2) of the material 12 is automatically detected as discussed above. More specifically, in decision block 58 (FIG. 3), it is determined whether the load detector 35 detects a load increase indicative of the probe surface 26 contacting the material 12. If this initial load increase is not detected (decision block 58 answered negatively), then the probe 24 continues actuating toward the material 12 in block 56. However, once the probe surface 26 contacts the material 12, block 60 follows, and the position detector 33 detects the distance between the probe surface 26 and the base surface 18 to determine the thickness $t_1$ of the material 12.

Next follows a plurality of cycles 65, 67, 69 of compression and release of the test material 12. Compression data and other data is gathered during one or more of these cycles 65, 67, 69. For instance, in some embodiments, the method 50 includes a first cycle 65 in which the material 12 is compressed to the thickness h (in block 62) and subsequently released (in block 64).

Then, in a second cycle 67, the material 12 is compressed to the thickness $t_2$ (in block 68), and in block 70, the compression load on the material 12 at thickness h is detected by the load detector 35 and this data is recorded in the memory module 34. Subsequently, in block 72, the material 12 is released from compression.

A third cycle 69 follows in which the material 12 is compressed to the thickness $t_2$ (in block 74), and in block 76, the load detector 35 and timer 38 cooperate to detect a change in compression load over a predetermined amount of time. More specifically, the probe 24 can hold the material 12 to the thickness $t_2$ for a predetermined amount of time (e.g., ten to sixty seconds) as measured by the timer 38, and the load detector 35 can detect a change in the compression load over this amount of time, for instance, to measure the viscoelasticity of the material 12. Then, the probe 24 can actuate away from and release the material 12 in block 78.

Next, in some embodiments, the assembly 10 can detect a recovery characteristic of the material 12 in block 80. For instance, the probe 24 can actuate to a distance from the base surface 18 approximately equal to the thickness $t_1$ (FIG. 2) and the timer 38 can detect the amount of time that elapses before the material 12 regains its full thickness $t_1$ and contacts the probe surface 26. The load detector 35 can detect a load increase when the material regains this full thickness $t_1$, and the timer 38 can detect how long it takes before this load is detected to detect the recovery time of the material 12.

In other embodiments, these recovery characteristics are detected in other ways. For instance, after the material 12 is released in block 78, the probe 24 can actuate toward the material 12 in predetermined stepped intervals until the load detector 35 detects a load increase (i.e., until the probe 24 contacts the material 12), and the thickness of the material (between $t_1$ and $t_2$) at that point can be detected to determine how the material 12 recovers after being compressed.

As stated above, the assembly 10 can perform compression testing on multiple portions of the material 12. Thus, in decision block 82, it is determined whether another portion of the material 12 is to be tested. If so (block 82 answered affirmatively), then block 84 follows, and the probe 24 is actuated in the X and/or Y direction over another portion of the material 12. Then, the method 50 returns to block 56 so that compression testing can be repeated for the corresponding portion of the material 12.

Once the material 12 has been tested completely (block 82 answered negatively), then the method 50 is completed, and data can be compiled and/or stored in the memory module 34. This data can be accessed across the network 44 as discussed above. Also, the alarm 40 can activate if the material 12 does not meet predetermined compression standards (either locally and/or remotely across the network 44) such that the material 12 can be discarded, recycled, re-tested, etc.

It will be appreciated that the method 50 can include any suitable number of cycles 65, 67, 69 of compression, data gathering, and releasing. Also, the method 50 can include a single cycle 65, 67, 69. Moreover, it will be appreciated that compression load data, viscoelasticity, recovery characteristics, and/or other data can be gathered during any of the cycles 65, 67, 69.

Accordingly, it will be appreciated that the testing assembly 10 and the method 50 of using the assembly 10 can allow for relatively quick and convenient compression testing. Also, it will be appreciated that the testing assembly 10 and the method 50 of its use can allow for accurate compression testing.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A compression testing assembly for compression testing of a test material, the compression testing device comprising:
    a testing stage including a first surface and a second surface, the test material being disposed between the first and second surfaces;
    a thickness detector that automatically detects a thickness of the test material;
    an actuator that moves at least one of the first and second surfaces toward the other of the first and second surfaces;
    a controller operable to control the actuator according to the thickness detected by the thickness detector, the controller operable to control the actuator to compress the test material to a predetermined percentage of the thickness of the test material as detected by the thickness detector; and
    a load detector that detects a compression load of the test material and that detects a change in the compression load over time,
    wherein the test material defines a thickness direction, wherein the actuator is operable to move the at least one of the first and second surfaces toward the other of the first and second surfaces in a first direction that is substantially parallel to the thickness direction to compress the test material, wherein the actuator is operable to move the at least one of the first and second surfaces relative to each other in a second direction that is perpendicular to the first direction to compress a first portion and a second portion of the test material, the first and second portions being separated at a distance in the second direction.

2. The compression testing assembly of claim 1, wherein the actuator moves the at least one of the first and second surfaces toward and away from the other of the first and second surfaces to compress and release the test material over a plurality of cycles including a first cycle and at least one subsequent cycle, the load detector configured to detect the compression load and the change in the compression load from the at least one subsequent cycle.

3. The compression testing assembly of claim 2, wherein the load detector is configured to detect the compression load and the change in the compression load over time from different subsequent cycles.

4. The compression testing assembly of claim 1, wherein the predetermined percentage of the thickness is between approximately thirty and seventy percent of the thickness of the test material as detected by the thickness detector.

5. The compression testing assembly of claim 4, wherein the predetermined percentage of the thickness is approximately fifty percent of the thickness of the test material as detected by the thickness detector.

6. The compression testing assembly of claim 1, further comprising a memory device for storing data, the data including at least one of the compression load and the change in the compression load over time.

7. The compression testing assembly of claim 1, further comprising a communications device for communicating over a communications network at least one of the compression load and the change in the compression load over time.

8. The compression testing assembly of claim 1, further comprising an alarm that outputs an alarm signal if at least one of the compression load and the change in the compression load over time is outside a respective predetermined limit.

9. A compression testing assembly for compression testing of a test material, the compression testing device comprising:
    a testing stage including a first surface and a second surface, the test material being disposed between the first and second surfaces;
    a thickness detector that automatically detects a thickness of the test material;
    an actuator that moves at least one of the first and second surfaces toward the other of the first and second surfaces;
    a controller operable to control the actuator according to the thickness detected by the thickness detector, the controller operable to control the actuator to compress the test material to a predetermined percentage of the thickness of the test material as detected by the thickness detector; and a load detector that detects a compression load of the test material and that detects a change in the compression load over time, wherein the actuator is operable to move the at least one of the first and second surfaces relative to the other of the first and second surfaces to compress the test material and to subsequently release the test material from compression, and wherein the load detector is configured to detect a recovery characteristic of the test material after the test material has been released from compression.

10. The compression testing assembly of claim 9, wherein the actuator is operable to space the first surface relative to the second surface at a distance approximately equal to the thickness detected by the thickness detector after the test material has been released from compression, and wherein the load detector is configured to detect the recovery characteristic when the test material regains the thickness detected by the thickness detector.

11. The compression testing assembly of claim 9, wherein the actuator, in a subsequent actuation, is operable to move the at least one of the first and second surfaces toward the other of the first and second surfaces after the test material has been released from compression, and wherein the load detector is configured to detect the recovery characteristic in association with the subsequent actuation.

12. The compression testing assembly of claim 11, wherein the actuator, in the subsequent actuation, is operable to move the at least one of the first and second surfaces toward the other of the first and second surfaces in a plurality of stepped movements, and wherein the load detector is configured to detect the recovery characteristic in association with one of the plurality of stepped movements.

13. A method of performing a compression test on a test material comprising:

disposing the test material between a first surface and a second surface;

actuating at least one of the first and second surfaces toward the other of the first and second surfaces;

automatically detecting a thickness of the test material;

compressing the test material between the first and second surfaces according to the detected thickness of the test material by compressing the test material to a predetermined percentage of the detected thickness of the test material;

detecting a compression load of the test material;

detecting a change in the compression load over time; and actuating the at least one of the first and second surfaces toward and away from the other of the first and second surfaces to compress and release the test material over a plurality of cycles including a first cycle and at least one subsequent cycle, and wherein detecting the compression load and detecting the change in the compression load occurs during the at least one subsequent cycle.

14. The method of claim 13, wherein detecting the compression load and detecting the change in the compression load over time occurs during different subsequent cycles.

15. A method of performing a compression test on a test material comprising:

disposing the test material between a first surface and a second surface;

actuating at least one of the first and second surfaces toward the other of the first and second surfaces;

automatically detecting a thickness of the test material;

compressing the test material between the first and second surfaces according to the detected thickness of the test material by compressing the test material to a predetermined percentage of the detected thickness of the test material;

detecting a compression load of the test material; and detecting a change in the compression load over time;

wherein actuating the at least one of the first and second surfaces toward the other of the first and second surfaces includes actuating the at least one of the first and second surfaces toward the other of the first and second surfaces in a first direction that is substantially parallel to a thickness direction of the test material to compress the test material, and further comprising actuating at least one of the first and second surfaces relative to each other in a second direction that is substantially perpendicular to the first direction, compressing a first portion of the test material, and compressing a second portion of the test material, the first and second portions being separated at a distance in the second direction.

16. The method of claim 15, wherein compressing the test material between the first and second surfaces to a predetermined percentage of the detected thickness of the test material includes compressing the test material between the first and second surfaces to a predetermined percentage between approximately thirty and seventy percent of the thickness of the test material.

17. The method of claim 15, further comprising communicating over a communications network at least one of the compression load and the change in the compression load over time.

18. The method of claim 15, wherein automatically detecting a thickness of the test material includes detecting a distance between the first and second surfaces when the compression load initially increases as the first and second surfaces are relatively moving toward each other.

* * * * *